US004001750B2

United States Statutory Invention Registration [19]

[11] Reg. Number: H1750

Dobrin

[45] Published: Sep. 1, 1998

[54] ABSORBENT ARTICLE HAVING A BREATHABLE BACKSHEET

[76] Inventor: George Christopher Dobrin, The Procter & Gamble Company, Winton Hill Technical Center, 6100 Center Hill Ave., Cincinnati, Ohio 45224

[21] Appl. No.: 812,225

[22] Filed: Mar. 6, 1997

[51] Int. Cl.[6] ..... A61F 13/00

[52] U.S. Cl. ..... 604/383

[58] Field of Search ..... 604/378, 383

[56] References Cited

U.S. PATENT DOCUMENTS

| | | | |
|---|---|---|---|
| 3,426,754 | 2/1969 | Bierenbaum . | |
| 3,881,489 | 5/1975 | Hartwell . | |
| 3,989,867 | 11/1976 | Sisson . | |
| 4,014,341 | 3/1977 | Karami . | |
| 4,306,559 | 12/1981 | Nishizawa et al. . | |
| 4,324,246 | 4/1982 | Mullane et al. . | |
| 4,341,216 | 7/1982 | Obenour . | |
| 4,341,217 | 7/1982 | Ferguson et al. . | |
| 4,342,314 | 8/1982 | Radel et al. . | |
| 4,395,215 | 7/1983 | Bishop . | |
| 4,578,069 | 3/1986 | Whitehead et al. . | |
| 4,609,584 | 9/1986 | Cutler et al. | 604/383 |
| 4,681,578 | 7/1987 | Anderson et al. | 604/385 R |
| 4,681,793 | 7/1987 | Linman et al. | 428/138 |
| 4,713,069 | 12/1987 | Wang et al. | 604/378 |
| 4,747,991 | 5/1988 | Bishop . | |
| 4,795,454 | 1/1989 | Dragoo . | |
| 4,842,596 | 6/1989 | Kielpikowski et al. . | |
| 4,872,871 | 10/1989 | Proxmire et al. . | |
| 4,887,602 | 12/1989 | O'Leary . | |
| 4,900,317 | 2/1990 | Buell . | |
| 4,908,026 | 3/1990 | Sukiennik et al. . | |
| 4,983,450 | 1/1991 | Yanagihara et al. . | |
| 5,069,678 | 12/1991 | Yamamoto et al. . | |
| 5,085,654 | 2/1992 | Buell . | |
| 5,098,423 | 3/1992 | Pieniak et al. . | |

(List continued on next page.)

FOREIGN PATENT DOCUMENTS

| | | |
|---|---|---|
| 0 477 802 A1 | 4/1992 | European Pat. Off. . |
| 2 699 812 | 7/1994 | France . |
| 2 268 389 | 1/1994 | United Kingdom . |
| 2 295 322 | 5/1996 | United Kingdom . |
| WO 95/17867 | 7/1995 | WIPO . |

*Primary Examiner*—Charles Jordan
*Assistant Examiner*—Meena Chelliah

[57] ABSTRACT

A disposable absorbent article having a breathable laminate backsheet. The absorbent article has a front waist region, a rear waist region, a crotch region positioned between the front waist region and the rear waist region, a pair of opposed side edges, a first end edge and a second end edge. The absorbent article includes an absorbent core having a pair of opposing longitudinal edges, a garment-facing side and a body-facing side, and a breathable laminate backsheet disposed adjacent to the garment-facing side of the absorbent core. The breathable laminate backsheet has an inner layer and an outer layer joined to one another. The inner layer is positioned between the absorbent core and the outer layer. The outer layer is relatively vapor pervious. The inner layer is substantially liquid impermeable and substantially vapor pervious. The inner layer is longitudinally coterminous with the absorbent article and of a smaller transverse width than the front waist region, the rear waist region, and the crotch region so as to form a breathable zone which is longitudinally coterminous with the absorbent article and adjacent to each of the side edges.

1 Claim, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS 5,158,819 10/1992 Goodman, Jr. et al. .
5,263,948 11/1993 Karami et al. ..... 604/383
5,263,949 11/1993 Karami et al. ..... 604/383
5,292,316 3/1994 Suzuki ..... 604/358
5,527,302 6/1996 Endres et al. .
5,558,658 9/1996 Menard et al. .
5,571,096 11/1996 Dobrin et al. .
5,628,737 5/1997 Dobrin et al. .
5,643,239 7/1997 Bodford et al. ..... 604/370
B1 4,636,207 11/1989 Buell .

ABSORBENT ARTICLE HAVING A BREATHABLE BACKSHEET

FIELD OF INVENTION

The present invention relates generally to disposable absorbent articles such as disposable diapers and, more particularly, to disposable absorbent articles having a breathable laminate backsheet.

BACKGROUND OF THE INVENTION

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. It is also known that the exterior of disposable diapers can be covered with a flexible, liquid and vapor impervious sheet to prevent any absorbed liquid from passing through the diaper and soiling adjacent articles such as clothing, bedding and the like. These outer covers, generally referred to as backsheets, are often constructed from fluid impervious films such as polyethylene. Although such backsheets do prevent liquid from passing through the diaper, they also can make the diaper feel hot and uncomfortable to wear because of their impermeability to air and/or moisture.

Backsheets which are pervious to vapor are generally known as breathable backsheets and have been described in the art. In general, these backsheets are intended to allow the passage of vapor through them while retarding the passage of liquid. For example, U.S. Pat. No. 3,156,242 issued to Crowe, Jr. on Nov. 10, 1964 teaches the use of a microporous film as a breathable backsheet. U.S. Pat. No. 3,881,489, issued to Hartwell on May 6, 1975, teaches a breathable backsheet comprising in combination two layers, the first of which is a low void volume perforated thermoplastic film and the second of which is a porous high void volume hydrophobic tissue. U.S. Pat. No. 3,989,867 issued to Sisson on Nov. 2, 1976 teaches a breathable backsheet provided with tapered hollowed bosses which prevent the passage of liquids while allowing vapors to pass readily therethrough.

While these backsheets do provide improvements over the impermeable backsheets of the prior art, comfort, dryness, and vapor exchange (breathability) remains as key design considerations. Accordingly, devices providing for better retention and absorption of liquids while providing for the more efficient passage of vapor have been sought.

Therefore, it is an object of the present invention to provide a disposable absorbent article having a breathable backsheet to ensure comfort for the wearer.

It is yet another object of this invention to provide a disposable absorbent article having a backsheet comprising zones of breathability, wherein the backsheet further comprises a vapor pervious and/or liquid pervious nonwoven web which provides the garment-facing surface of the backsheet with a cloth-like feel.

It is still another object of the present invention to provide a disposable absorbent article having good containment and breathability characteristics that is economical and easy to manufacture at high speeds.

SUMMARY OF THE INVENTION

A disposable absorbent article having a front waist region having a transverse width, a rear waist region having a transverse width, a crotch region having a transverse width positioned between the front waist region and the rear waist region, a pair of opposed side edges, a first end edge located in the front waist region and a second end edge located in the rear waist region. The absorbent article comprises an absorbent core having a pair of opposing longitudinal edges, a garment-facing side and a body-facing side and a breathable laminate disposed adjacent said garment-facing side of said absorbent core. The breathable laminate comprises an inner layer and an outer layer joined to one another. The inner layer is positioned between the absorbent core and the outer layer. The outer layer is relatively vapor pervious, and the inner layer is substantially liquid impermeable and substantially vapor pervious. The inner layer is longitudinally coterminous with said absorbent article and of a smaller transverse width than the transverse width of said front waist region, said rear waist region, and said crotch region so as to form a breathable zone which is longitudinally coterminous with said absorbent article and adjacent to each of said side edges.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
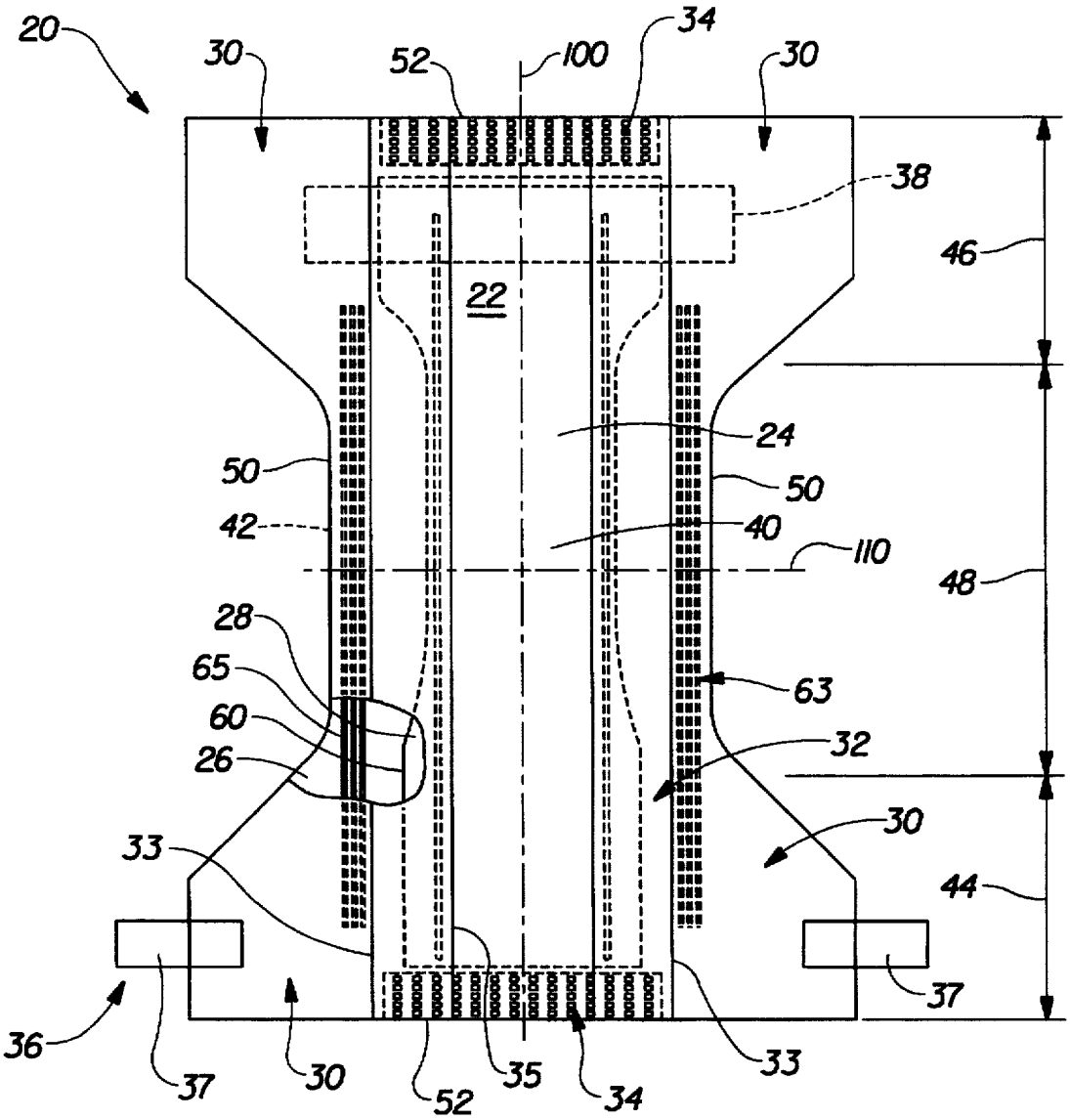
FIG. 1 is a plan view of a disposable diaper embodiment of the present invention having portions cut away to reveal underlying structure, the inner surface of the diaper is facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid pervious topsheet 24; a laminate backsheet 26 joined to the topsheet; and an absorbent core 28 positioned between the topsheet 24 and the laminate backsheet 26. The absorbent core 28 has a pair of opposing longitudinal edges 60, a body-facing side 62 and a garment-facing side 64. The diaper preferably further comprises side panels 30; elasticized leg cuffs 32; elasticized waistbands 34; and a fastening system 36 preferably comprising a pair of securement members 37 and a landing member 38.

The diaper 20 is shown in FIG. 1 to have an inner surface 40 (facing the viewer in FIG. 1), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side or longitudinal edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the laminate backsheet 26 and other components joined to the laminate backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 preferably comprises a topsheet 24, a laminate backsheet 26 and an absorbent core 28 having a pair of opposing longitudinal edges 60, a body-facing side 62, and a garment-facing side 64. The body-facing side 62 generally faces the body of the wearer while the garment-facing side 64 generally faces away from the body of the wearer. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a laminate backsheet, and an absorbent core.) For unitary absorbent articles, the containment assembly 22 preferably comprises the topsheet 24, the backsheet 26 and the absorbent core 28 of the diaper with other features added to form the composite diaper structure.

FIG. 1 shows a preferred embodiment of the containment assembly 22 in which the topsheet 24 and the laminate backsheet 26 have length and width dimensions generally larger than those of the absorbent core 28. The topsheet 24 and the laminate backsheet 26 extend beyond the edges of the absorbent core 28 to thereby form the periphery of the diaper 20. While the topsheet 24, the laminate backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side 64, a body-facing side 62, a pair of side edges 60, and a pair of waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 24 is preferably positioned adjacent the body-facing side 62 of the absorbent core 28 and is preferably joined thereto and to the laminate backsheet 26 by attachment means (not shown) such as those well known in the art. Suitable attachment means are described with respect to joining the laminate backsheet 26 to the absorbent core 28. In a preferred embodiment of the present invention, the topsheet 24 and the laminate backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

An alternative preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

The laminate backsheet 26 of the present invention is that portion of the diaper 20 which is generally positioned away from the wearer's skin and which prevents the exudates absorbed and contained in the absorbent core 28 from wetting articles which contact the diaper 20 such as bedsheets and undergarments.

The laminate backsheet 26 is preferably positioned adjacent the garment-facing side 64 of the absorbent core 28 and is preferably joined thereto by any suitable attachment means known in the art. For example, the laminate backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Embodiments of the present invention are also contemplated wherein the absorbent core 28 is not joined to the laminate backsheet 26, and/or the topsheet 24 in order to provide greater extensibility especially in the front waist region 46 and the rear waist region 44.

Figure 2:
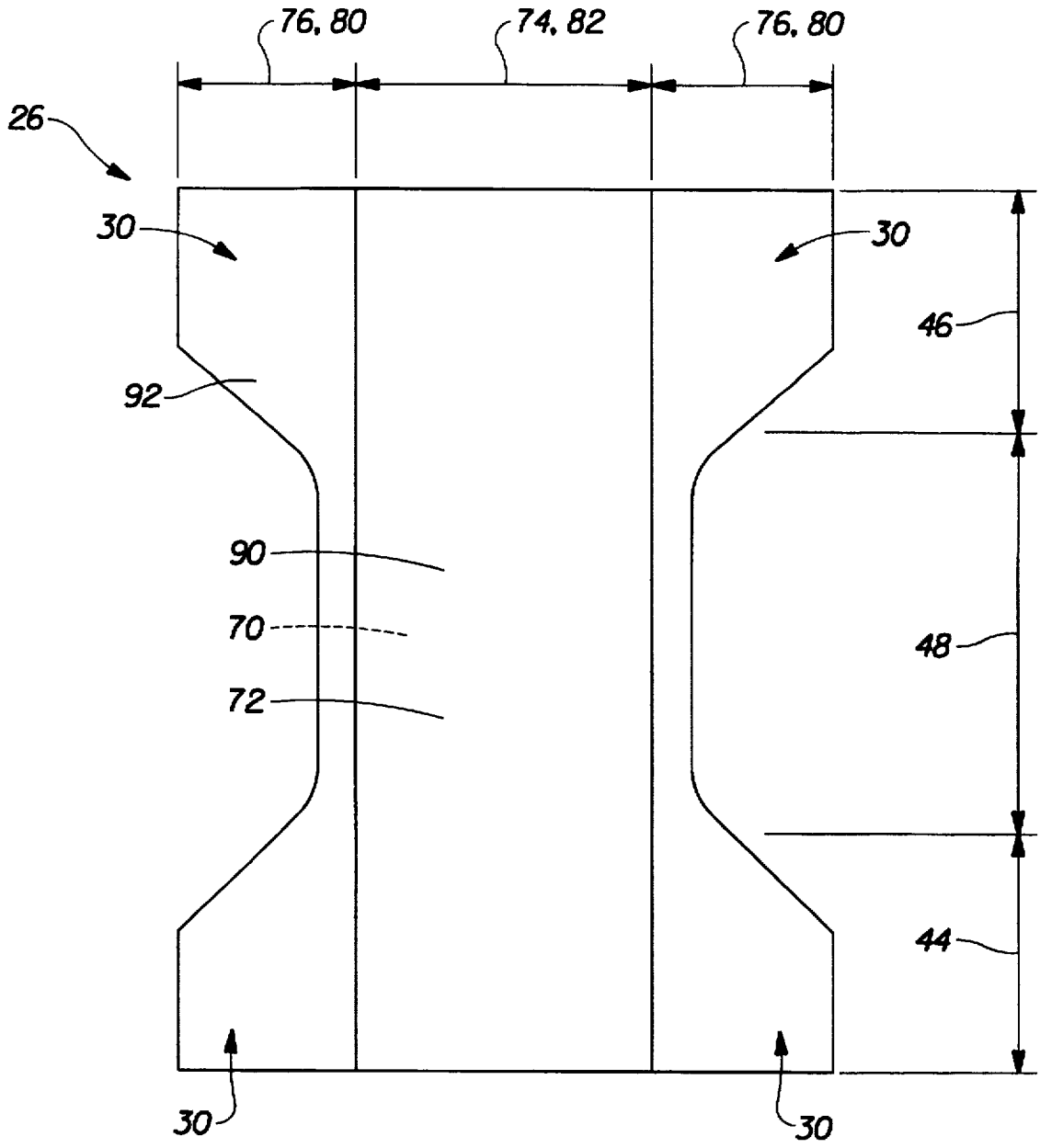
FIG. 2 is a plan view of a laminate backsheet suitable for use in the diaper of the present invention with the body-facing side of the backsheet facing the viewer.
Figure 3:
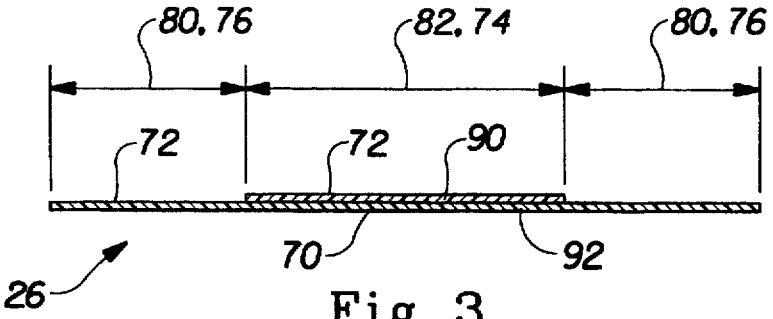
FIG. 3 is an enlarged, cross-sectional view of the laminate backsheet of FIG. 2.

The laminate backsheet 26 of the present invention, as shown in FIGS. 2–3, comprises an inner layer 90 and an outer layer 92 joined to one another. The means by which the inner layer 90 and the outer layer 92 are joined to one another include any means known in the art such as adhesives, heat, pressure, heat and pressure, extrusion, and ultrasonic bonds. The laminate backsheet 26 has a body-facing side 72, a garment-facing side 70, a central region 74 and two outer regions 76. Further, the laminate backsheet 26 comprises at least three distinct zones, a first breathable zone 82, and two opposing second breathable zones 80. The first breathable zone 82 preferably comprises the central region 74 of the laminate backsheet 26 and is juxtaposed at least a portion of the garment-facing side 64 of the absorbent core 28. The first breathable zone 82 provides a substantially liquid impermeable structure that contains the liquids that have passed into the containment assembly 22. In a preferred embodiment, the first breathable zone 82 covers the entire garment-facing side 64 of the absorbent core 28. (As used herein, the term "covers" means that one member is generally, either directly or indirectly in a face-to-face relationship with another member.) In an especially preferred embodiment, the first breathable zone 82 not only covers the garment-facing side 64 of the absorbent core 28, but also extends laterally outwardly to at least any location at which any barrier cuffs (described below) that may be joined to the diaper 20, such as the proximal edge 33 of the barrier cuffs 32. (As used herein, the term "laterally outwardly" refers to a direction away from the longitudinal centerline 100.) This insures that any liquid absorbed by the absorbent core 28 or otherwise deposited into the containment assembly 22 of the diaper 20 will not seep through the second breathable zones 80 of the laminate backsheet 26.

The outer layer 92 preferably comprises a nonwoven web. However, embodiments are contemplated wherein the outer cover 92 comprises materials such as woven webs, foams, scrims, films, or any other material or combination of materials known in the art that would give the diaper a clothlike look and/or feel and is at a minimum air permeable. The outer layer 92 covers the entire laminate backsheet 26 thereby forming the periphery of the diaper 20. In addition, the nonwoven web of the outer layer 92 provides the diaper with a cloth-like look and feel. Further, the outer layer 92 may provide the diaper with a low cost landing zone capable of engaging hook and loop type fasteners. Such a landing zone could be utilized as a portion of a primary fastening system or as a means for disposing of a soiled diaper.

The nonwoven web of the outer layer 92 is liquid and air pervious to allow free vapor passage in the second breathable zones 80. The nonwoven web may comprise natural fibers (e.g., cotton or wood fibers), or may comprise fibers of polyethylene, polypropylene, polyester, or any combination of such fibers. Further, the nonwoven web may be carded, spun melt, meltblown, or air-through bonded or have any other characteristic or be manufactured in any manner known in the art. Preferably, the nonwoven web is comprised of sufficient thermoplastic material to allow for thermal bonding of the nonwoven web to other components of the diaper. An especially preferred nonwoven web is a carded nonwoven web made of 100% polypropylene fibers such as FPN 290 manufactured by FiberWeb North America of Simpsonville, S.C. It may be desirable, however, to provide an outer layer 92 that acts to change the perviousness (either vapor or liquid) in certain regions of the second breathable zones 80. Such may be the case in disposable article designs wherein the second breathable zones 80 underlie or are otherwise in contact with any portion of the article which may absorb liquids. In such cases, it may be desirable to use a hydrophobic nonwoven web to help prevent any leakage of the liquids from the article.

Interposed between the absorbent core 28 and the outer layer 92 is inner layer 90. The inner layer 90 prevents fluids retained by the absorbent core 28 from striking through the diaper 20 and soiling adjacent garments. Therefore, the inner layer 90 must be at least substantially fluid impervious and preferably, completely fluid impervious. Suitable materials are well known in the art, include woven and nonwoven fabrics which have been treated to render them liquid-repellent. Breathable or vapor pervious liquid resistant materials, and those materials described in U.S. Pat. No. 3,881,489 issued to Hartwell on May 6, 1975 and U.S. Pat. No. 3,989,867 issued to Sisson on Nov. 2, 1976 can also be used. These patents are incorporated herein by reference.

The size of the inner layer 90 is a key factor in forming the first breathable zone 82 and the second breathable zones 80. The size and shape of the inner layer 90 generally determines the size, shape, and location of the first breathable zone 82 and the second breathable zones 80. While the inner layer 90 is longitudinally coterminous with (i.e., the same length as) the diaper 20, the inner layer 90 has a smaller transverse width than the transverse width of the diaper 20 in the front waist region 46, the rear waist region 44 and the crotch region 48 so that a second breathable zone 80 is formed in the diaper 20 which is longitudinally coterminous with the diaper 20. Therefore, the inner layer 90 may generally be of any shape and size that conforms to the above description to permit the laminate backsheet 26 to have two opposed second breathable zones 80 which are longitudinally coterminous with the diaper 20.

While the inner layer 90 is longitudinally coterminous with the outer layer 92, the inner layer 90 has a smaller transverse width than that of the outer layer 92 in all regions of the diaper, i.e., the front waist region 46, the rear waist region 44, and the crotch region 48 so that a second breathable zone 80 is formed in the backsheet 26 which is longitudinally coterminous with the backsheet 26.

A preferred shape of the inner layer 90 is shown in FIG. 2. The inner layer 90 has a uniform transverse width. In addition, the inner layer has a uniform transverse width which is smaller than the narrowest portion of the crotch region 48 of the diaper 20. With this configuration two opposed second breathable zones 80 are formed which are longitudinally coterminous with the diaper 20.

For disposable absorbent articles, and particularly for garments such as diapers which are form-fitting such as those disclosed herein, the breathability exhibited by the backsheet has been found critical to the performance of the absorbent article especially in hot and humid conditions. When an absorbent article is positioned on a wearer, the skin is occluded by the materials making up the absorbent article. This occlusion of the skin, especially in hot and humid conditions, prevents evaporation and resulting cooling of the occluded area. The resultant perspiration raises the relative humidity of air inside of the absorbent article resulting in less comfort for the wearer and perceived negative benefits by caregivers. In addition, incidents of heat rash and other negative skin macerations can increase if the absorbent article does not have sufficient capability to move the water vapor created by the body out of the absorbent article.

Conventional diapers have attempted to use breathable materials to reduce the humidity within the diaper. However, these materials have not provided sufficient moisture vapor transmission rates to reduce the humidity inside the product to an extent that provides the wearer comfort when exposed to hot and humid conditions.

It has been found that the moisture vapor transmission rate of the opposing second breathable zones 80 of the backsheet 26 in conjunction with the overall vapor transmission rate of the rest of the backsheet is important in reducing the incidents of heat rash and other skin problems associated with high heat and humidity conditions. In order to reduce humidity and heat build up within the absorbent article, it has been found that the second breathable zones 80 of the backsheet 26 should have a mass vapor transmission rate of at least about 2500 $g/m^2/24$ hr., more preferably at least about 3000 $g/m^2/24$ hr.

The central region 74 which comprises the first breathable zone 82 is substantially liquid impermeable to contain liquids absorbed by the absorbent core 28. Since the central region 74 comprising the first breathable zone 82 must contain liquids absorbed by the absorbent core it typically has a lower mass vapor transmission rate than the second breathable zones 80 which are not relied upon to contain any of the absorbed liquids. Accordingly, it has been found that the first breathable zone 82 is the main limiting factor in providing an overall absorbent article with a high average mass vapor transmission rate. However, it has been found that the first breathable zone 82 should have a mass vapor transmission rate of at least about 1500 $g/m^2/24$ hr., more preferably at least about 2000 $g/m^2/24$ hr. The first breathable zone 82 and thus the entire absorbent article, given the materials, would generally have a mass vapor transmission rate in a range at least from about 1500 $g/m^2/24$ hr. to about 8000 $g/m^2/24$ hr., more preferably from about 2000 $g/m^2/24$ hr. to about 7000 $g/m^2/24$ hr. Thus, it is preferred that each zone of the backsheet 26 should have a mass vapor transmission rate of at least about 1500 $g/m^2/24$ hr. As can be seen, because the first breathable zone 82 comprises both the inner layer 90 and the outer layer 92, it has an effective mass vapor transmission rate which is less than that of the second breathable zones 80 which comprise only the outer layer 92. This is expected as the first breathable zone 82 is responsible for retaining liquids absorbed by the absorbent core 28 from passing through the laminate backsheet 26 while the second breathable zones 80 of the laminate backsheet 26 do not need to assist in the containment of liquids within the disposable diaper 20.

The moisture vapor transmission rate is measured by the method set forth below. A known amount of $CaCl_2$ is put into a flanged cup. A sample is placed on the top of the cup and held securely by a retaining ring and gasket. The assembly is then weighed and recorded as the initial weight. The assembly is placed in a constant temperature (40° C.) and humidity (75% RH) chamber for 5 hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in $g/m^2/24$ hr. using the following formula:

$$MVTR = \frac{(\text{Final weight} - \text{initial weight}) \times 24.0}{\text{Area of sample in meters} \times 5.0(\text{time in chamber})}$$

In embodiments of the present invention comprising leg cuffs 32, as described below, the second breathable zones 80 may be disposed laterally inwardly or outwardly of the leg cuffs 32. Further, the second breathable zones 80 may form a portion of the leg cuffs 32. However, in a preferred embodiment, the second breathable zones 80 extend laterally outwardly from the proximal edge 33 of the leg cuffs 32. In another preferred embodiment of the present invention, the second breathable zones 80 extend laterally outwardly from a location that is laterally outboard of the proximal edge 33 of the leg cuff 32 and laterally inboard of the gasketing cuff 63. Such a configuration provides the diaper 20 with a liquid impervious gasketing seal about the legs of the wearer that prevents liquids from escaping the containment assembly 22 of the diaper 20. In yet another embodiment, the second breathable zones 80 extend laterally outwardly from a location laterally outboard of the gasketing cuff 63.

It may also be desirable to provide the disposable article of the present invention with extensibility or elasticity in all or a portion of the side panels 30. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 30 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 30 further provide more effective application of the diaper 20 since even if the diaperer pulls one side panel 30 farther than the other during the application (asymmetrically), the diaper 20 will "self-adjust" during wear. While the extensible side panels 30 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels 30, or any other elements of the diaper 20 in which extensibility or elasticity is desirable such as the waistbands 34 may comprise materials that have been "prestrained", or "mechanically prestrained" (i.e., subjected to some degree of localized pattern mechanical stretching to permanently elongate the material), or structure elastic-like webs (SELF), as described below. The materials may be prestrained using deep embossing techniques as are known in the art. Alternatively, the materials may be prestrained by directing the material through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the extensible side panels 30 or any portions of the side panels 30 or the materials included in the side panels or any other element of the diaper 20 in which extensibility is desirable may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages on controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention and the method for making such webs are more completely described in commonly assigned U.S. Pat. No. 5,518,801 entitled "Web Materials Exhibiting Elastic-Like Behavior", issued to Chappell, et al. on May 21, 1996, which is incorporated herein by reference.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. (Each of these patents are incorporated herein by reference.)

Figure 4:
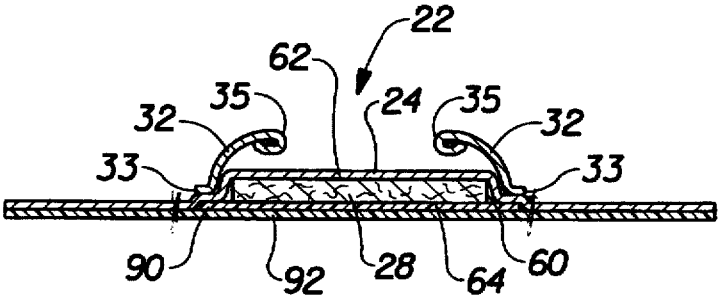
FIG. 4 an enlarged, cross-sectional view of one embodiment of a disposable absorbent article comprising the backsheet shown in FIGS. 2–3.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff comprising a barrier flap and a spacing element such as described in the above-referenced U.S. Pat. No. 4,909,803. In a preferred embodiment, the elasticized leg cuff 32 additionally comprises an elastic gasketing cuff 63 with one or more elastic strands 65, positioned outboard of the barrier cuff such as described in the above-referred U.S. Pat. No. 4,695,278. Further, as shown in FIG. 4, the elasticized leg cuff 32 preferably has a proximal edge 33 and a distal edge 35. The distal edge 35 of the elasticized leg cuff 32 is that part of the elasticized leg cuff 32 which is spaced away from the chassis 22 of the diaper when the diaper 20 is being worn. The proximal edge 33 is that part of the elasticized leg cuff 32 which is joined to the chassis 22 of the diaper 20. The proximal edge 33 is generally located laterally inboard of the periphery of the diaper 20. A portion of the elasticized leg cuff 32, however, may extend laterally outwardly from the proximal edge 33 such that the material covers at least a portion of the outer region 76 of the backsheet 26. (not shown). An example of an elasticized cuff 32 having a portion extending laterally outwardly over most or all of the outer region 76 of the backsheet 26 is described in the above-referenced U.S. Pat. No. 4,795,454 issued to Dragoo, which is hereby incorporated by reference herein.

The diaper 20 preferably further comprises an elasticized waistband 34 that provides improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges of the absorbent core 28 and generally forms at least a portion of the end edge of the diaper 20. Disposable diapers are generally constructed so as to have two elasticized waistbands, one positioned in the rear waist region and one positioned in the front waist region, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. The elasticized waistband 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a front waist region having a transverse width, a rear waist region having a transverse width, a crotch region having a transverse width positioned between the front waist region and the rear waist region, a pair of opposed side edges, a first end edge located in said front waist region and a second end edge located in said rear waist region, said absorbent article comprising:

an absorbent core having a pair of opposing longitudinal edges, a garment-facing side and a body-facing side; and a breathable laminate disposed adjacent said garment-facing side of said absorbent core, said breathable laminate comprising an inner layer and an outer layer joined to one another, said inner layer being positioned between said absorbent core and said outer layer, said outer layer being relatively vapor pervious, said inner layer being substantially liquid impermeable and substantially vapor pervious, said inner layer being longitudinally coterminous with said absorbent article and of a smaller transverse width than the transverse width of said front waist region, said rear waist region, and said crotch region so as to form a breathable zone which is longitudinally coterminous with said absorbent article and adjacent to each of said side edges.

* * * * *